US009445983B2

United States Patent
Hayakawa et al.

(10) Patent No.: US 9,445,983 B2
(45) Date of Patent: Sep. 20, 2016

(54) AQUEOUS MANICURE COMPOSITION

(71) Applicant: MITSUBISHI PENCIL COMPANY, LIMITED, Shinagawa-ku (JP)

(72) Inventors: Takayuki Hayakawa, Fujioka (JP); Satoshi Sakuma, Fujioka (JP); Yukako Shinmura, Fujioka (JP); Mitsuo Azuma, Yao (JP); Yosuke Ikemoto, Yao (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/026,563

(22) Filed: Sep. 13, 2013

(65) Prior Publication Data

US 2014/0079654 A1   Mar. 20, 2014

(30) Foreign Application Priority Data

Sep. 14, 2012 (JP) ................................ 2012-202359

(51) Int. Cl.
| | | |
|---|---|---|
| *A61K 8/81* | (2006.01) | |
| *A61K 8/06* | (2006.01) | |
| *A61Q 3/02* | (2006.01) | |
| *A61K 8/26* | (2006.01) | |
| *A61K 8/02* | (2006.01) | |

(52) U.S. Cl.
CPC ........... *A61K 8/8152* (2013.01); *A61K 8/0241* (2013.01); *A61K 8/06* (2013.01); *A61K 8/26* (2013.01); *A61Q 3/02* (2013.01); *A61K 2800/654* (2013.01); *A61K 2800/87* (2013.01)

(58) Field of Classification Search
CPC ......... A61K 8/8152; A61K 8/06; A61Q 3/02
See application file for complete search history.

(56) References Cited

U.S. PATENT DOCUMENTS

| 6,296,858 B1 * | 10/2001 | Agostini et al. ............... 424/401 |
|---|---|---|
| 7,538,148 B2 | 5/2009 | Inoue et al. |
| 7,721,402 B2 | 5/2010 | Inoue et al. |
| 7,914,222 B2 | 3/2011 | Inoue et al. |
| 2002/0061319 A1 * | 5/2002 | Bernard et al. ............... 424/401 |

(Continued)

FOREIGN PATENT DOCUMENTS

| JP | 55-108309 A | 8/1980 |
|---|---|---|
| JP | 2000-026240 A | 1/2000 |

(Continued)

OTHER PUBLICATIONS

Opinion of the Scientific Committee for Animal Nutritionon the use of titanium dioxide-coated mica in feedingstuffs for salmon and trout: retrieved from internet: http://ec.europa.eu/food/fs/sc/scan/out117_en.pdf. retrieved on Sep. 29, 2014.*

Wong et al.: Breadth of Glass Transition Temperature in Styrene/Acrylic Acid Block, Random, and Gradient Copolymers: Unusual Sequence Distribution Effects, Journal of Polymer Science: Part B: Polymer Physics, vol. 45, p. 2842-2849, 2007.*

(Continued)

*Primary Examiner* — Ernst V Arnold
*Assistant Examiner* — Hong Yu
(74) *Attorney, Agent, or Firm* — Buchanan, Ingersoll & Rooney PC

(57) ABSTRACT

Provided is an aqueous manicure composition by which three-dimensional patterns and shapes can freely be formed in an one-liquid, wherein the shapes are maintained after drying, and make-up such as a nail art can easily be enjoyed. The above aqueous manicure composition is characterized by containing at least an acrylic resin emulsion, a thickener and an extender.

4 Claims, 5 Drawing Sheets

(56) References Cited

U.S. PATENT DOCUMENTS

| | | |
|---|---|---|
| 2006/0233595 A1 | 10/2006 | Inoue et al. |
| 2006/0260112 A1 | 11/2006 | Inoue et al. |
| 2007/0110507 A1 | 5/2007 | Inoue et al. |
| 2007/0207096 A1* | 9/2007 | Puisset et al. .................. 424/61 |
| 2011/0222956 A1* | 9/2011 | Hayakawa et al. ........... 401/198 |

FOREIGN PATENT DOCUMENTS

| | | | |
|---|---|---|---|
| JP | 2001-039831 A | 2/2001 | |
| JP | 2007-217411 A | 8/2007 | |
| JP | 2008-247036 A | 10/2008 | |
| JP | 2010-195689 A | 9/2010 | |
| JP | 3166632 U | 3/2011 | |
| WO | WO 2010/055838 A1 * | 5/2010 | ............... A61K 8/73 |

OTHER PUBLICATIONS

Nylon density: retrieved from internet: http://www.matweb.com/search/datasheet.aspx?matguid=c24aea7f07ca4020bea255513d3f5bd3&ckck=1. retrieved on Sep. 29, 2014.*

Polyacrylate density: retrieved from internet: http://www.google.com/url?sa=t&rct=j&q=&esrc=s&frm=1&source=web&cd=3&ved=0CC8QFjAC&url=http%3A%2F%2Fwww.chem.indiana.edu%2Ffaculty-research%2Ffaculty-resources%2Fchemistry-demos%2Fdemos%2F16DensityBlocks.doc&ei=NMz9VMrTCcOMNu7CgKAJ&usg=AFQjCNETuvAs7OsYg_xQjRruiusVIMbOTQ&bvm=bv.87611401,d.eXY. Retrieved on Mar. 9, 2015.*

* cited by examiner

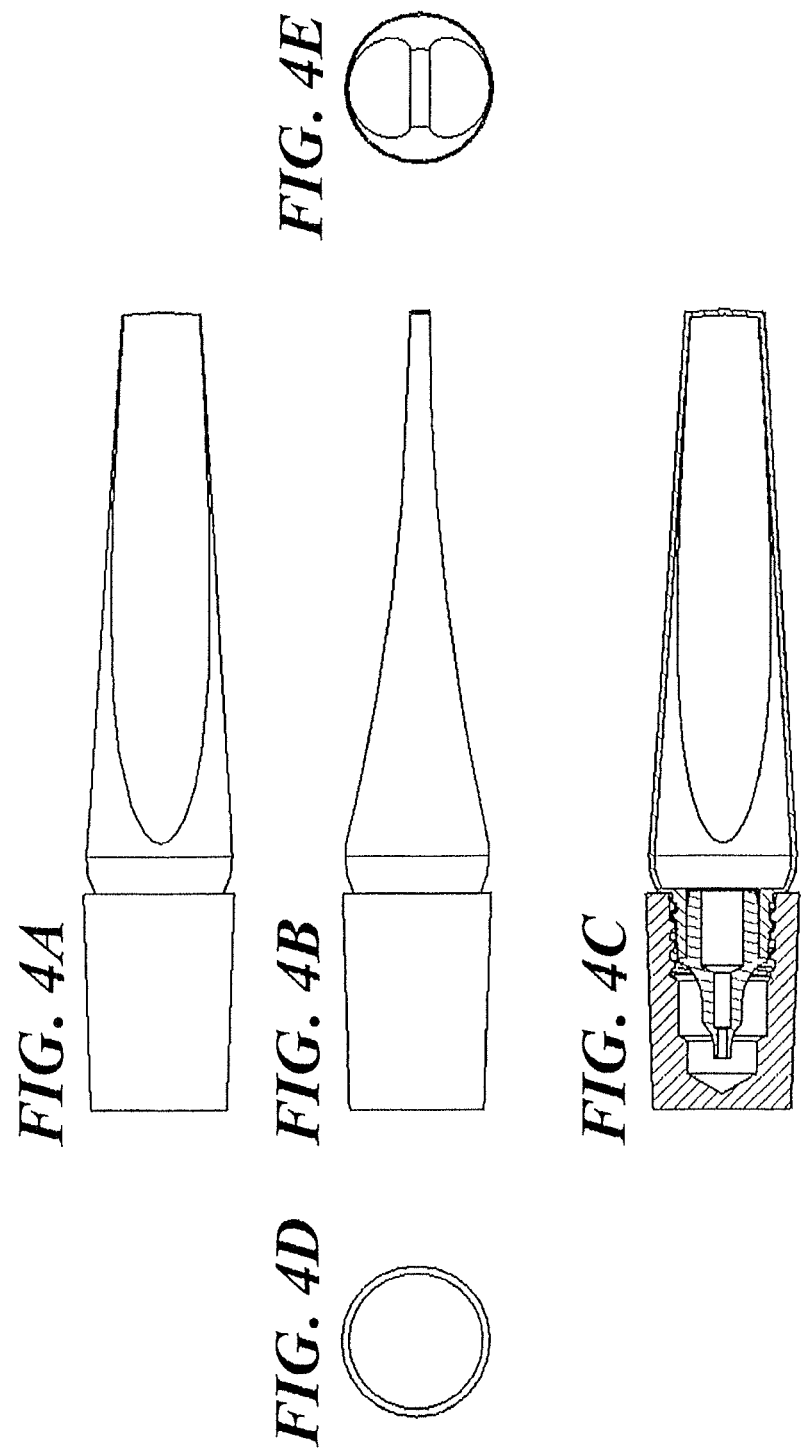

AQUEOUS MANICURE COMPOSITION

This Nonprovisional application claims priority under 35 U.S.C. §119(a) on Patent Application No. 2012-202359 filed in Japan on Sep. 14, 2012, the entire contents of which are hereby incorporated by reference.

BACKGROUND OF THE INVENTION

1. Field of the Invention

The present invention relates to an aqueous manicure composition by which three-dimensional patterns and shapes can readily be formed, more specifically to an aqueous manicure composition by which three-dimensional patterns and shapes can freely be formed in an one-liquid, wherein the shapes are maintained after drying, and make-up such as a nail art can easily be enjoyed.

2. Description of Related Art

Various methods have so far been employed for providing three-dimensional patterns and decorations in a nail art.

In general, known as a method for providing nail art with three-dimensional decorations made of stone and resin is a method in which they are fixed thereon by using such as topcoats for a nail enamel and adhesive resins.

However, in a method in which three-dimensional stones are stuck, quick works therefor have to be carried out before the adhesive resin is dried, and delicate works carried out using such as tweezers are required. Further, various sized kits have to be provided for arts.

Also, it is carried out as well to form three-dimensional decorations by a composition prepared by mixing an acrylic resin powder with an acrylic monomer liquid curing at an ambient temperature in a technique of an acrylic nail (sculptured nail) (refer to, for example, patent document 1).

However, in the acrylic nail composition described in patent document 1, the acrylic monomer is used and therefore involves problems in terms of health and safety, and in addition thereto, a skilled technique for mixing the acrylic monomer liquid with the acrylic resin powder has been required.

Further, known is a writing instrument (refer to, for example, patent document 2) in which an aqueous ink composition containing a viscous synthetic resin emulsion as a three-dimensional film forming component is received and by which three-dimensional handwritings can be formed.

On the other hand, known as a method for providing three-dimensional decorations on a nail are a method in which decorations are molded by pouring a polyvinyl chloride paste into a molding die (refer to, for example, patent document 3) and a method in which decorations are molded by inserting a visible light-curing resin into a transparent molding die and cured by irradiation of a visible light (refer to, for example, patent document 4).

However, in the respective art disclosed in patent documents 2 to 4, three-dimensional patterns and shapes can not freely be formed in an one-liquid, and the problem that disturbs to enjoy nail arts freely is involved therein.

On the other hand, known is a manicure liquid composition which is odorless and safe and which is prepared by blending an aqueous emulsion as an organic binder with fine powders of shells (refer to, for example, patent document 5). However, it is neither described nor suggested to provide three-dimensional decorations by the above manicure liquid composition.

Also, a highly viscous nail varnish composition containing clay minerals is known (refer to, for example, patent document 6). However, the above composition has a strong odor due to use of an organic solvent and can form a even and smooth coating film, but it is not suited to forming three-dimensional patterns and shapes.

Further, known is an aqueous manicure composition (refer to, for example, patent document 6) prepared by mixing a clay mineral base gelatinizer with an aqueous emulsion polymer by means of a specific disperser. The above aqueous manicure composition provides the excellently even coating film and gives an excellent durability and an excellent gloss to the make-up, but it is neither described nor suggested to provide three-dimensional decorations.

Patent document 1: Japanese Patent Application Laid-Open Sho 55 No. 108309 (Claims, Examples, and others)
Patent document 2: Japanese Patent Application Laid-Open No. 2008-247036 (Claims, Examples, and others)
Patent document 3: Japanese Utility Publication No. 3166632 (Claims, Drawings, and others)
Patent document 4: Japanese Patent Application Laid-Open No. 2001-39831 (Claims, Examples, and others)
Patent document 5: Japanese Patent Application Laid-Open No. 2010-195689 (Claims, Examples, and others)
Patent document 6: Japanese Patent Application Laid-Open No. 2007-217411 (Claims, Examples, and others)
Patent document 7: Japanese Patent Application Laid-Open No. 2000-26240 (Claims, Examples, and others)

SUMMARY OF THE INVENTION

In light of the foregoing problems of the conventional art, an object of the present invention is to solve them and provide an aqueous manicure composition by which three-dimensional patterns and shapes can freely be formed in an one-liquid type, wherein the shapes are maintained after drying, and make-up such as a nail art can easily be enjoyed.

In light of the conventional problems described above, intense researches repeated by the present inventors have resulted in finding that an aqueous manicure composition by which three-dimensional shapes are maintained after drying is obtained by preparing an aqueous manicure composition containing at least a specific resin emulsion, a thickener and an extender, and thus the present invention has come to be completed.

That is, the present invention resides in the following items (1) to (7).

(1) An aqueous manicure composition containing at least an acrylic resin emulsion, a thickener and an extender.
(2) The aqueous manicure composition as described in the above item (1), wherein the thickener is a clay mineral, and the extender is a resin powder.
(3) The aqueous manicure composition as described in the above item (1), containing 3 to 50% by mass of the resin emulsion in terms of a solid content, 0.001 to 2% by mass of the thickener and 7 to 45% by volume of the extender.
(4) The aqueous manicure composition as described in the above item (1), wherein a viscosity in a shear rate of 3.83 $(s^{-1})$ is 1000 to 20000 (mPa·s) at 25° C.
(5) The aqueous manicure composition as described in the above item (1), containing the acrylic resin having a glass transition temperature of 50° C. or higher as the acrylic resin emulsion.
(6) The aqueous manicure composition as described in the above item (1), further containing a film forming auxiliary agent.
(7) The aqueous manicure composition as described in the above item (1), wherein it comprises an one-liquid.

According to the present invention, provided is an aqueous manicure composition by which three-dimensional patterns and shapes can freely be formed in an one-liquid, wherein the shapes are maintained after drying, and make-up such as a nail art can easily be enjoyed.

BRIEF DESCRIPTION OF THE DRAWINGS

FIGS. 4A to 4E are (4A) a plan view, (4B) a side view, (4C) a sectional view, (4D) a front view and (4E) a rear view in an assembly outline drawing of the applicator 2 filled with the aqueous manicure composition of the present invention.

DETAILED DESCRIPTION OF THE PREFERRED EMBODIMENTS

Figure 1:
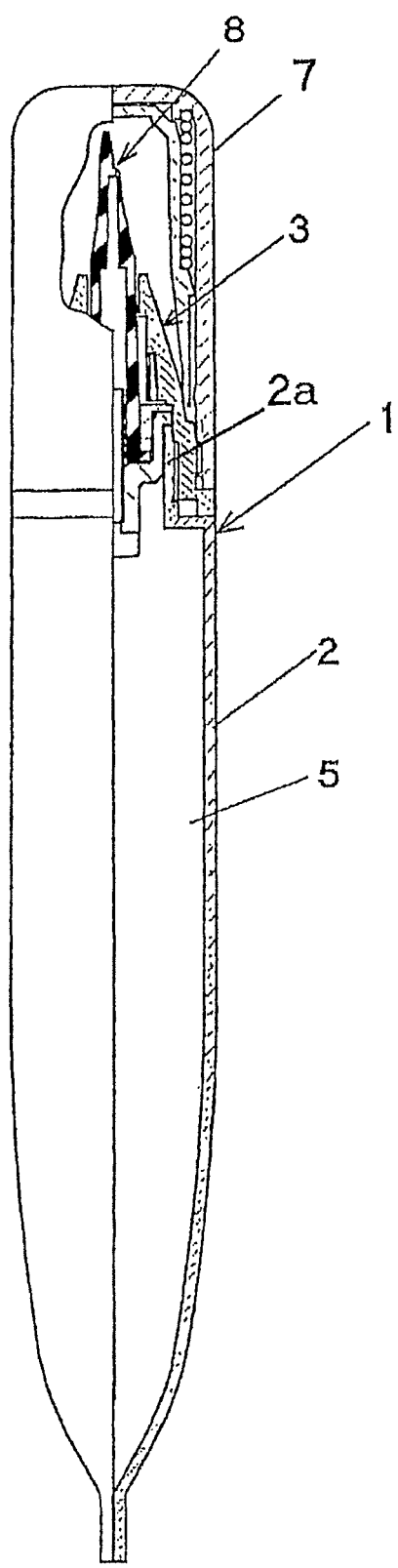
FIG. 1 is a partial vertical cross-sectional drawing showing a first embodiment (hereinafter referred to as an applicator 1) of an applicator filled with the aqueous manicure composition of the present invention.

The embodiments of the present invention shall be explained below in detail.

The aqueous manicure composition of the present invention is characterized by containing at least an acrylic resin emulsion, a thickener and an extender.

The acrylic resin emulsion used in the present invention is added for the purpose of forming steric shapes.

The usable acrylic resin emulsion includes, for example, such as alkyl acrylate copolymer emulsions, acrylate ester-methacrylate ester copolymer emulsions, and alkyl acrylate•styrene copolymer emulsions.

SE-2696F (manufactured by Taisei Fine Chemical Co., Ltd.) can be listed as the specific alkyl acrylate copolymer emulsions, and JONCRYL 352, 538J, 7640, 7641, 631, 790, 780 and 7610 (manufactured by BASF SE), SE-810A, SE-841A, SE-953A-2 and SE-1658F (manufactured by Taisei Fine Chemical Co., Ltd.) and Marposol C-1 (manufactured by Matsumoto Yushi-Seiyaku Co., Ltd.) can be listed as the alkyl acrylate•styrene copolymer emulsions. They can be used at least in one kind (each alone or in a mixture of two or more kinds thereof).

In the above acrylic resin emulsions, the acrylic resins having a glass transition temperature (Tg) of 50° C. or higher, 60 to 100° C. is preferably used from the viewpoint of a hardness and a shape retention after drying. In the present invention (including examples described later), the "glass transition temperature (Tg)" means a temperature at which when an amorphous solid matter is heated, a solid matter being as hard as a crystalline solid and having no fluidity at low temperature is reduced quickly in a rigidity and a viscosity in some narrow temperature range and is increased in a fluidity (temperature at which glass transition is brought about).

A content of the above acrylic resin emulsions is 3 to 50% by mass (hereinafter referred to merely as "%") in terms of a solid content, preferably 5 to 50%, more preferably 5 to 35% and particularly preferably 10 to 30% based on a total amount of the aqueous manicure composition.

If the above content is less than 3%, the resin amount enough for forming three-dimensional shapes is not obtained. On the other hand, if it exceeds 50%, it is difficult to blend other components, and the physical properties are varied to a large extent due to vaporization of water in storing and using. Accordingly, both are not preferred.

The thickener used in the present invention is added for the purpose of increasing the viscosity.

The thickener which can be used includes, for example, at least one of clay minerals such as synthetic smectite and bentonite, natural polysaccharides, and acrylic polymers, and the like.

The specific synthetic smectite includes Lucentite SWN (manufactured by Co-op Chemical Co., Ltd.); the bentonite includes Bengal FW (manufactured by HOJUN Co., Ltd.); the polysaccharides include xanthan gum and the like.

The synthetic smectite is preferably used as the preferred thickener from the viewpoint of dispersibility and an aging stability.

A content of the above thickeners is 0.001 to 2% in terms of a solid content, preferably 0.01 to 1% based on a total amount of the aqueous manicure composition.

If the above content is less than 0.001%, the required viscosity is not obtained. On the other hand, if it exceeds 2%, the viscosity is increased too much, and therefore the usability is deteriorated.

The extender used in the present invention is added for the purpose of maintaining the three-dimensional shapes.

The extender which can be used includes, for example, at least one of resin powders such as acrylic resin powders and urethane resin powders, silica, talc, kaolin, mica, synthetic mica, sericite, magnesium carbonate, calcium carbonate, cellulose beads, and the like.

Listed is at least one of MP-2200 (manufactured by Soken Chemical & Engineering Co., Ltd.) and Matsumoto Micro Sphere M-100 and M-101 (manufactured by Matsumoto Yushi-Seiyaku Co., Ltd.) as the specific acrylic resin powder, Aerosil 200 and 380 (manufactured by Nippon Aerosil Co., Ltd.) as silica and RonaFlair Mica M (manufactured by Merck KGaA) as mica.

The acrylic resin powder is preferably used as the preferred extender from the viewpoint of compatibility with the resin emulsion.

The above extender is contained in the aqueous manicure composition in a proportion of 7% by volume or more, preferably 7 to 45% by volume, more preferably 8 to 40% by volume and particularly preferably 10 to 30% by volume based on the aqueous manicure composition.

If the above extender is contained in a proportion of less than 7% by volume, it is difficult to maintain the three-dimensional shapes. On the other hand, if it exceeds 45% by volume, an amount of the extender is too large, and the fluidity is lost. Accordingly, both are not preferred.

In the present invention (including examples described later), "% by volume" means a proportion of the extender based on a total volume of the cosmetic.

The aqueous manicure composition of the present invention contains the respective components described above, and it can contain, if necessary, a suited amount of a colorant in order to provide three-dimensional color patterns and color shapes.

Organic pigments, inorganic pigments, pearl pigments and other luster pigments which are usually used for cosmetics can be used as the usable colorant.

Capable of being listed as the organic pigments are Blue No. 1 Al lake, Red No. 202, Red No. 226, No. 228, Blue No. 404, Red No. 220, Yellow No. 401, Yellow No. 205, Blue No. 201, Blue No. 204, Yellow No. 4 Al lake, Yellow No. 203 Al lake, Red No. 104 Al lake, and the like. Prussian blue, red iron oxide, yellow iron oxide, black iron oxide, titanium oxide, and the like can be listed as the inorganic pigment. Capable of being listed as the pearl pigments are mica, mica titanium, carmine-coated mica titanium, carmine•Prussian blue-coated mica titanium, black iron oxide-coated mica titanium, black iron oxide•carmine-coated mica titanium, black iron oxide•Prussian blue-coated mica titanium, Prussian blue-coated mica titanium, red iron oxide-coated mica, red iron oxide-coated mica titanium, red iron oxide•carmine-coated mica titanium, red iron oxide•black iron oxide-coated mica titanium, red iron oxide•Prussian blue-coated mica titanium, red iron oxide•black iron oxide•Prussian blue-coated mica titanium, and the like.

Also, the aqueous manicure composition of the present invention can contain water (refined water, distilled water, deionized water, purified water and the like) as the balance. Further, water-soluble organic solvents and other optional components, for example, resin emulsions such as (acrylate/ethylhexyl acrylate copolymers) can be used for the purpose to control the drying property.

The usable organic solvent includes, for example, alcohols such as ethanol, phenoxyethanol, and 2-propanol, and glycols such as 1,3-butylene glycol.

The above organic solvent is added in a proportion of 0 to 20%, preferably 0.1 to 20% based on a total amount of the aqueous manicure composition in order to obtain the suitable drying property.

Further, a film forming auxiliary agent can be used for the aqueous manicure composition of the present invention for the purpose of enhancing a film forming property of the acrylic resin emulsion described above.

The usable film forming auxiliary agent includes, for example, at least one selected from such as diethoxydiglycol, diethylene glycol diethyl ether, propylene carbonate, diethylene glycol monobutyl ether, propylene glycol monomethyl ether (PGM), and diethylene glycol monoethyl ether.

The above film forming auxiliary agent is added in a proportion of 0 to 10%, preferably 0.1 to 10% based on a total amount of the aqueous manicure composition from the viewpoint of further enhancing a film forming property of the acrylic resin emulsion.

The aqueous manicure composition of the present invention has a viscosity of 1000 to 20000 (mPa·s), preferably 3000 to 7000 (mPa·s) in a shear rate of 3.83 ($s^{-1}$) at 25° C. from the viewpoint of forming the three-dimensional shapes.

If the above viscosity is less than 1000 (mPa·s), the cosmetic flows, and the three-dimensional shapes are ruptured in a certain case. On the other hand, if it exceeds 20000 (mPa·s), the cosmetic is too sticky and cause the three-dimensional shapes to be provided with edges.

The viscosity range described above can be controlled by suitably combining such as the acrylic resin emulsion, the thickener, the extender, and water and effectively combining them in the ranges of the contents described above.

The aqueous manicure composition of the present invention can be prepared by an ordinary method, and it is filled in an applicator and coated on such as a nail.

The usable applicator shall not specifically be restricted as long as a suitable amount of the aqueous manicure composition can be coated on such as a nail in the form of optional shapes and characters. Capable of being listed are, for example, applicators mounted in bottle vessels and tube vessels each equipped with a discharge port such as a pipe at a tip thereof.

Figure 2A:
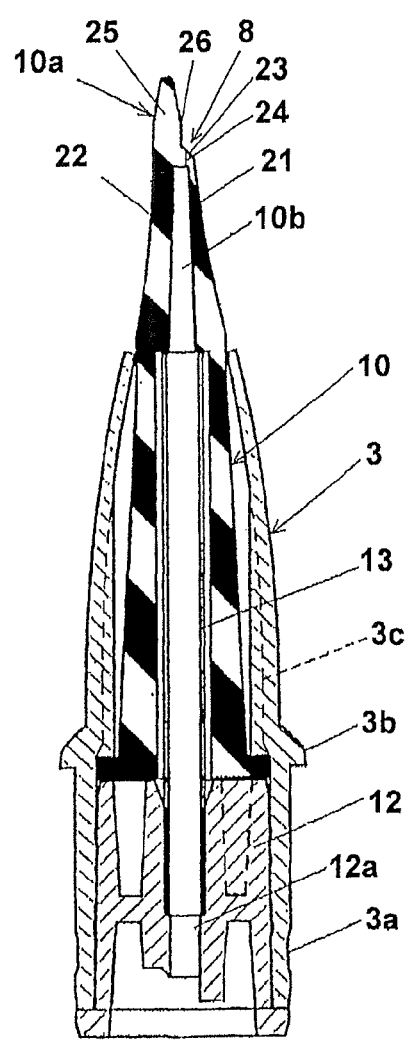
FIGS. 2A to 2C are (2A) a side cross-sectional drawing, (2B) a plan view of a half cross section and (2C) a drawing observing from an axial direction each showing a structure of a front barrel part of the applicator 1 filled with the aqueous manicure composition of the present invention.
Figure 2B:
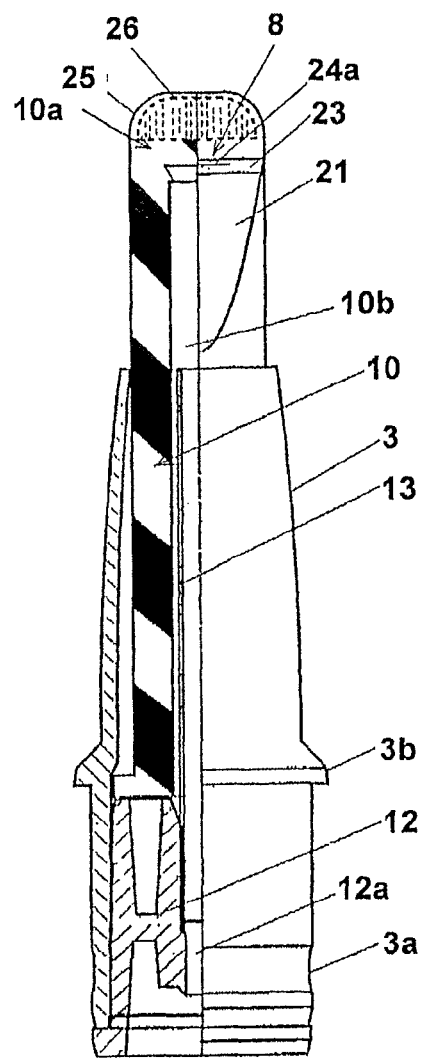
Figure 2C:
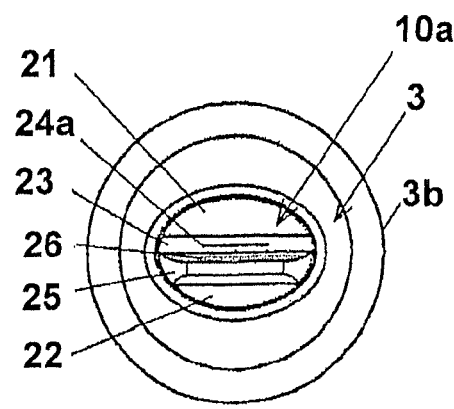
Figure 5:
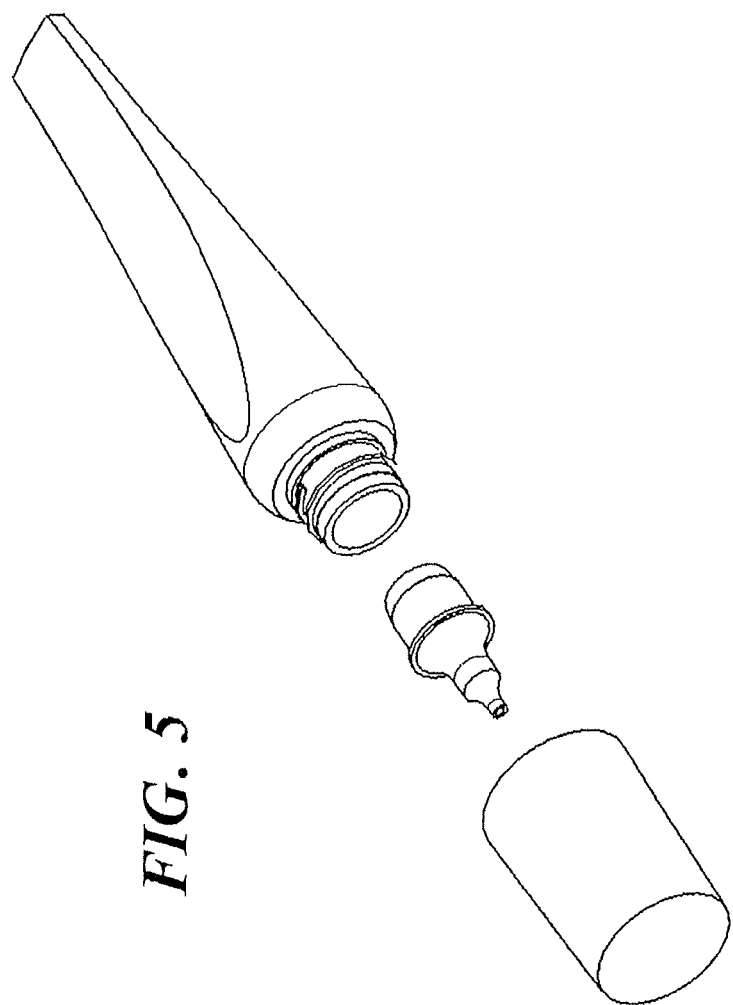
FIG. 5 is a deal perspective drawing of the applicator 2 filled with the aqueous manicure composition of the present invention.

To be specific, a first embodiment, an applicator 1 shown in FIG. 1 and FIG. 2, and a second embodiment, an applicator 2 shown in FIG. 3 to FIG. 5 can be listed for coating arbitrary shapes and patterns.

The above applicator 1 is equipped, as shown in FIG. 1 and FIG. 2, with a manual liquid pressing mechanism, and the aqueous manicure composition of the present invention (hereinafter referred to merely as the "coating liquid") charged in a main body 2 is supplied to an applying member 10 via a valve mechanism 8 by pressing the liquid pressing mechanism.

The above applicator 1 comprises, as shown in FIG. 1, the main body 2 which is an outside holder, a front barrel 3, a liquid pressing mechanism, a cap 7 and the valve mechanism 8 as principal members.

Also, the cap 7 is formed by a double cap and protects the structure of the front barrel 3 in a more sealed manner. The valve mechanism 8 of the applying member 10 comprises a mechanism shown in FIG. 2.

The applying member 10 of the applicator 1 comprises an elastic material, and a communication passage 24 communicating to an inside and an outside of the main body 2 is formed, wherein the applying member 10 has the valve mechanism 8 which closes the communication passage 24 in a normal state (state of not pressing the coating liquid) and which can elastically deform and open the communication passage 24 when the coating liquid is pressurized by the liquid pressing mechanism, and an applying part 10a of the applying member 10 is provided in a form of protruding further from a discharge port 24a of the communication passage 24 in the valve mechanism 8 toward a tip thereof.

The main body 2 shows a hollow cylindrical form in which one end is sealed, wherein a small size part 2a is formed at a tip part thereof, and the cap 7 is detachably interlocked with the small size part.

A base end of the front barrel 3 is inserted and fixed in an opening of the small size part 2a in the main body 2, and a manual liquid pressing mechanism is arranged at a rear end of the main body 2.

As shown in FIG. 2, the front barrel 3 is formed in a cylindrical structure of a tapering form in which a diameter is decreased toward a tip thereof. The applying member 10 is received in an inside space of the front barrel 3 opened at both front and rear ends thereof in a state in which a tip part thereof is protruded, and the applying member 10 is fixed to the main body 2 in the received state. The applying member 10 presents a form in which it becomes flatter and narrower, as described later, toward a front side thereof.

A circular interlocking concave part 3a is formed on a rear side periphery of the front barrel 3. The interlocking concave part 3a is pressed and inserted into a circular interlocking convex part (not illustrated) formed on an inner surface of the small size part 2a in the main body 2 to prevent the front barrel 3 from being left out from the main body 2.

Further, a handguard 3b is formed on a periphery of the front barrel 3 and brought into contact with a front end surface of the small size part. Plural ribs 3c extending to an axial direction are formed on an inner surface of the front barrel 3 at an equal interval on the inner peripheral surface, and a flange-shaped part which is increased in a diameter at a rear end part of the applying member 10 is interposed by a rear end part of the ribs 3c and a front end part of a pipe joint 12 so that the applying member 10 is inserted and fixed in the front barrel 3.

The applying member 10 comprises an elastic member and is supported by the pipe joint 12 and a coating liquid supplying pipe 13. The coating liquid supplying pipe 13 is inserted and fixed in a through hole 12a at the center of the pipe joint 12, and it is inserted from a rear end part of a hole part 10b provided in the applying member 10 into an intermediate part (a tip part of the front barrel 3) which is a large size part of the hole part and acts also as a liquid leaking inhibition mechanism.

The applying member 10 comprises tapered parts 21, 22 on both surfaces and assumes a flat and tapered shape. A step is formed in the tapered part 21 of an upper surface, and the valve mechanism 8 is provided at a shoulder part 23 thereof. The applying part 10a of the applying member 10 is formed further protruding from the manual valve mechanism toward the tip.

The valve mechanism comprises a simple mechanism operated by making use of an elastic deformation of the communication passage 24 formed on the shoulder part 23 in a slit shape and the applying part 10a. The communication passage 24 is communicated with the hole part 10b of the applying member 10, and it is closed by an elastic force thereof in an ordinary state so that the coating liquid does not flow out to the outside. On the other hand, when the coating liquid is pressed by the liquid pressing mechanism, the communication passage 24 is opened by an elastic deformation thereof.

In the above applicator 1, a whole part of the applying member 10 may comprise an elastic member, or only the applying part 10a may be composed of an elastic member. Elastic materials such as rubbers, and elastomers can be listed as the material of the applying member 10. Any materials can be used as the material of the applying member 10 without any problems as long as it has a liquid seal, for example, it is an elastic member having no open cells.

The material includes, for example, (1) rubbers such as NBR, silicone rubbers, EPDM, fluorosilicone rubbers, fluorocarbon rubbers, urethane rubbers, natural rubbers, chloroprene rubbers, butadiene rubbers, and butyl rubbers, (2) elastomers such as styrene base elastomers, vinyl chloride base elastomers, olefin base elastomers, polyester base elastomers, polyamide base elastomers, and urethane base elastomers and (3) closed-cell members such as polyethylene foams, vinyl chloride foams, and polystyrene foams.

As shown in FIG. 2, the applying part 10a is a part further extending from the shoulder part 23 on which a step is formed, and it is formed as a plane part 25, wherein a rough surface part 26 is formed on the plane part 25. The coating liquid discharged from the discharge port 24a of the communication passage 24 is temporarily held once on the rough surface part 26 of the plane part 25.

In the applicator 1 constituted in the manner described above, the coating liquid is filled in the main body, the pipe joint of the front barrel 3, the coating liquid supplying pipe 13 and the hole part 10b of the applying member 10 in an ordinary state. The communication passage 24 stays in a closed state, and therefore the coating liquid is not exposed to the outside air. Also, the coating liquid is pressed by the manual liquid pressing mechanism in use. The communication passage 24 of the valve mechanism 8 is opened resisting an elastic force thereof by pressing the coating liquid. This operation causes the coating liquid to be discharged in a prescribed amount, and the communication passage 24 is closed by causing the coating liquid to balance almost with the atmospheric pressure.

Even if the coating liquid discharged runs out a little, it is temporarily held on the rough surface part 26 present extending at a tip of the plane part 25, and it is derived to and coated on a soft coating surface such as a skin. After finishing coating, the coating liquid staying on the plane part 25 is readily wiped off by such as facial tissues, and wastes.

In non-use, the valve mechanism 8 prevents fungi from penetrating in an ordinary state. On the other hand, in pressing, the closed communication passage 24 is elastically deformed and opened to discharge the coating liquid from the discharge port 24a, and the applicator can smoothly be used. Also, the plane part 25 (liquid holding part) for temporarily holding the discharged coating liquid is provided in the discharge port 24a of the communication passage 24 in the applying part 10a, whereby the coating liquid can be prevented from blobbing due to quickly running out.

As can be found from the above, the coating liquid exposed to the outside air after used is limited to a range of the discharge port 24a to the applying part 10a and can readily be removed, and therefore the coating liquid of the present invention which falls in a suitable viscosity range not only can readily be coated, but also the coating liquid stored in the applicator can sufficiently be protected from a microbial contamination coming in from the air and the outside.

In the applicator 1 equipped with the manual liquid pressing mechanism described above, the coating liquid is pressurized in the main body 2 by lightly pressing the main body 2 with a finger, and the coating liquid deforms the slit-shaped communication passage 24 and is discharged to the plane part 25 (temporarily liquid holding part). Also, even when the main body 2 is pressed a little excessively, the coating liquid is temporarily held on the plane part 25 and therefore prevented from blobbing. Further, a liquid decompression mechanism for decompressing the coating liquid is constituted by releasing pressing after pressed, so that the valve mechanism 8 of the communication passage 24 is forcibly closed.

In the present invention, when the user draws such as arbitrary shapes (patterns and others) and characters on a nail, with the aqueous manicure composition of the present invention from an applying tip of the applicator described above, three-dimensional patterns and shapes can be freely formed in an one-liquid. Thus, obtained is the aqueous manicure composition by which the shapes are maintained after drying, and make-up such as a nail art can easily be enjoyed.

Figures 3A, 3B, 3C:
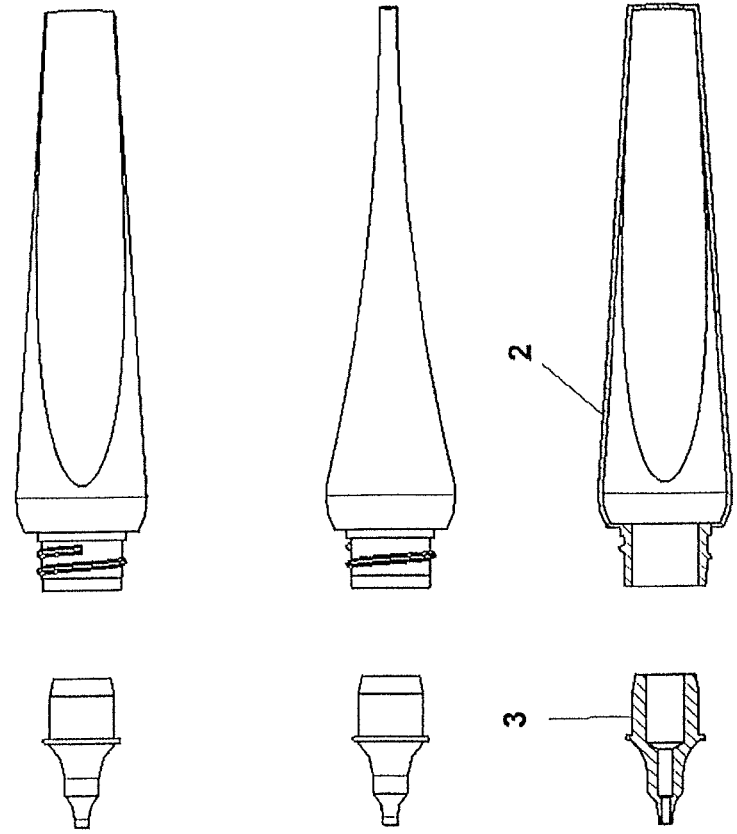
FIGS. 3A to 3C are (3A) a plan view, (3B) a side view and (3C) a sectional view of a deal drawing in a second embodiment (hereinafter referred to as an applicator 2) of an applicator which is filled with the aqueous manicure composition of the present invention and which is suited to drawing narrow lines.

Next, the applicator 2 comprises, as shown in FIG. 3C, the main body 2, the front barrel 3 and the cap 7, and the coating liquid stored in an inside of the main body 2, which is different in a shape, is supplied, as is the case with the applicator 1, to an applying member at a tip of the front barrel 3 by pressing the manual liquid pressing mechanism. The tip of the applying member is provided with a shape suited to drawing narrow lines which is different from the applicator 1. The cap 7 is detachably connected with a screw part at the tip of the applying member by screwing to prevent the coating liquid from being dried in non-use and protect the tip of the applying member.

Next, the present invention shall be explained in further details with reference to examples, but the present invention shall not be restricted by the examples shown below.

Examples 1 to 12 and Comparative Examples 1 to 3

The components were mixed and dispersed in blend compositions (total amount: 100%) shown in the following Table 1 by means of a planetary stirring device, a planetary mixer, a homomixer or a disperser to prepare the respective manicure compositions.

The respective manicure compositions obtained in Examples 1 to 12 and Comparative Examples 1 to 3 described above were used to evaluate the respective viscosities of 25° C. at a shear rate of 3.83 ($s^{-1}$), a molding property, a three-dimensional shape holding property, a drying property and an aging stability by the following methods. The results thereof are shown in the following Table 1.

Measuring Method of Viscosity:

The respective manicure compositions obtained were used to measure a viscosity in a prescribed shear rate at a temperature of 25° C. by means of a corn plate type viscometer (among TV-30 viscometers, an EHD type viscometer or a standard corn plate type viscometer manufactured by Tokimec Inc.).

Evaluation Method of Molding Property:

The respective manicure compositions about 0.5 μl were coated on a film (hereinafter referred to as a manicure coating film) prepared by coating a conventional nail enamel on a glass plate and drying, and an easiness of molding a shape was evaluated according to the following criteria:

Evaluation Criteria:

○: spherical or hemispherical droplets were formed

Δ: three-dimensional shapes were formed, but they were ruptured hemispherical, or they were not spherical, and edges were formed X: three-dimensional shapes could not be formed Evaluation Method of Three-Dimensional Shape Holding Property:

The respective manicure compositions about 0.5 μl were mounted on the manicure coating film to measure a height of the shape from the coating film, and after 10 minutes, the height from the coating film was measured again and compared with that in the initial state to evaluate it according to the following criteria:

Evaluation Criteria:

○: height after 10 minutes was 80% or more of the initial height

Δ: height after 10 minutes was 70 to 79% of the initial height

X: height after 10 minutes was 69% or less of the initial height

Evaluation Method of Drying Property:

The respective manicure compositions about 0.5 μl were put on the manicure coating film to evaluate a finger-touch drying speed; to be specific, time elapsed until the liquid came to be unstuck to a finger by touching and was not ruptured by applying a small force was confirmed to evaluate it according to the following criteria:

Evaluation Criteria:

○: 5 minutes or shorter

ΔA: 5 to 10 minutes

X: 10 minutes or longer

Evaluation Method of Aging Stability:

The respective manicure compositions were stored in a thermostatic bath of 50° C. for 1 month, and then a viscosity value thereof was measured and evaluated according to the following criteria:

Evaluation Criteria:

○: scarcely changed from the viscosity value (initial value) immediately after produced and stable Δ: fluctuated to some extent from the viscosity value (initial value) immediately after produced, but no influence was exerted on the usability X: increased or decreased very much in a viscosity from the viscosity value (initial value) immediately after produced, and the usability was different to a large extent from that in the beginning

TABLE 1

| | | Example | | | | | | | |
|---|---|---|---|---|---|---|---|---|---|
| | | 1 | 2 | 3 | 4 | 5 | 6 | 7 | 8 |
| Solvent | 1,3-Butylene glycol | 5 | | | | | | | 5 |
| Solvent | Phenoxyethanol | 0.6 | 0.6 | 0.6 | 0.6 | 0.6 | 0.6 | 0.6 | 0.6 |
| Solvent | Ethanol | | 3 | 3 | 3 | 3 | 5 | 5 | |
| Solvent | Water | 17.1 | 16.04 | 15.04 | 15.99 | 15.99 | 14.1 | 15.1 | 17.1 |
| Thickener | Synthetic smectite*1 | 0.3 | 0.36 | 0.36 | 0.36 | 0.36 | 0.3 | 0.3 | 0.3 |
| Resin | Acrylic resin emulsion*2 | 55 | 55 | 55 | 55 | 55 | 60 | 60 | 20 |
| Resin | Resin emulsion*3 | 2 | 5 | 5 | 5 | 5 | 5 | 5 | 2 |
| Film-forming auxiliary agent | Diethylene glycol diethyl ether | 5 | 5 | 5 | 5 | 5 | 5 | 5 | 5 |
| Extender | Acrylic resin powder*4 | 15 | 15 | 14 | 15 | 15 | 10 | 9 | 50 |
| Colorant | Red 202 | | | | 0.05 | | | | |
| Colorant | Red 228 | | | | | 0.05 | | | |
| Colorant | Colorona Precious Gold*5 | | | 2 | | | | | |
| Extender % by volume | | 12.5 | 12.5 | 11.7 | 12.5 | 12.5 | 8.3 | 7.5 | 41.7 |
| Viscosity (mPa · s) 1 rpm, 3.83 $s^{-1}$ | | 5650 | 5380 | 4120 | 3900 | 3720 | 2000 | 1800 | 20000 |
| Evaluation | Molding property | ○ | ○ | ○ | ○ | ○ | Δ | Δ | Δ |
| | 3D shape holding property | ○ | ○ | ○ | ○ | ○ | Δ | Δ | ○ |
| | Drying property | ○ | ○ | ○ | ○ | ○ | ○ | ○ | ○ |
| | Aging stability | ○ | ○ | ○ | ○ | ○ | ○ | ○ | Δ |

TABLE 1-continued

|  |  | Example | | | | Comparative Example | | |
| --- | --- | --- | --- | --- | --- | --- | --- | --- |
|  |  | 9 | 10 | 11 | 12 | 1 | 2 | 3 |
| Solvent | 1,3-Butylene glycol | 5 | 5 | 5 | 5 | 5 | 5 | 5 |
| Solvent | Phenoxyethanol | 0.6 | 0.6 | 0.6 | 0.6 | 0.6 | 0.6 | 0.6 |
| Solvent | Ethanol |  |  |  |  |  |  |  |
| Solvent | Water | 62.1 | 2.1 | 17.399 | 15.4 | 72.1 | 32.1 | 17.4 |
| Thickener | Synthetic smectite*1 | 0.3 | 0.3 | 0.001 | 2 | 0.3 | 0.3 |  |
| Resin | Acrylic resin emulsion*2 | 10 | 76 | 55 | 55 |  | 55 | 55 |
| Resin | Resin emulsion*3 | 2 | 2 | 2 | 2 | 2 | 2 | 2 |
| Film-forming auxiliary agent | Diethylene glycol diethyl ether | 5 | 5 | 5 | 5 | 5 | 5 | 5 |
| Extender | Acrylic resin powder*4 | 15 | 9 | 15 | 15 | 15 |  | 15 |
| Colorant | Red 202 |  |  |  |  |  |  |  |
| Colorant | Red 228 |  |  |  |  |  |  |  |
| Colorant | Colorona Precious Gold*5 |  |  |  |  |  |  |  |
| Extender % by volume |  | 12.5 | 7.5 | 12.5 | 12.5 | 12.8 | 0 | 12.8 |
| Viscosity (mPa · s) 1 rpm, 3.83 s$^{-1}$ |  | 1200 | 7000 | 1000 | 20000 | 1000 | 800 | 1000 |
| Evaluation | Molding property | Δ | Δ | Δ | Δ | X | X | X |
|  | 3D shape holding property | ○ | Δ | ○ | ○ | X | X | X |
|  | Drying property | Δ | ○ | ○ | ○ | Δ | ○ | ○ |
|  | Aging stability | ○ | Δ | ○ | ○ | ○ | ○ | ○ |

The items shown by *1 to *5 in TABLE 1 show the followings:
*1: Lucentite SWN, manufactured by CO-OP CHEMICAL CO., LTD.
*2: alkyl acrylate•styrene copolymer, glass transition templerature (Tg): 80° C., solid content: 40%
*3: DAITOSOL 4000SJT, acrylate/ethylhexyl acrylate copolymer, manufactured by DAITO KASEI KOGYO CO., LTD.
*4: MP2200, acrylic resin powder, manufactured by Soken Chemical & Engineering Co., Ltd.
*5: manufactured by Merck KGaA As apparent from the results shown in Table 1 described above, it has become confirmed that the manicure compositions prepared in Examples 1 to 12 according the present invention are excellent in a molding property, a three-dimensional shape holding property, a drying property and an aging stability as compared with the manicure compositions prepared in Comparative Examples 1 to 3 falling outside the present invention.

To individually observe the comparative examples, it has been found that in Comparative Example 1 in which the acrylic resin emulsion was not added, Comparative Example 2 in which the extender was not added and Comparative Example 1 in which the thickener was not added, the effects of the present invention can not be exerted.

The suitable aqueous manicure composition by which three-dimensional patterns and shapes can freely be formed on such as a nail in an one-liquid type is obtained.

The invention claimed is:

1. An aqueous manicure composition containing at least 3 to 50% by mass of an acrylic resin emulsion in terms of a solid content whose acrylic resin has glass transition temperature of 50° C. or higher, 0.001 to 1% by mass of a thickener, and 7 to 45% by volume of acrylic resin powder as an extender, wherein the aqueous manicure composition has a viscosity in a shear rate of 3.83 (s$^{-1}$) of 1000 to 20000 (mPa·s) at 25° C., and wherein the aqueous manicure composition is capable of forming a three-dimensional shape or pattern on a nail.

2. The aqueous manicure composition as described in claim 1, wherein the thickener is a clay mineral.

3. The aqueous manicure composition as described in claim 1, further containing a film forming auxiliary agent.

4. A method for forming a sculptured nail art having a three-dimensional shape or pattern by utilizing only a one-liquid composition of the aqueous manicure composition as described in claim 1.

* * * * *